(12) United States Patent
Colley et al.

(10) Patent No.: US 7,553,397 B1
(45) Date of Patent: *Jun. 30, 2009

(54) PROCESS (75) Inventors: Stephen William Colley, Dormanstown (GB); Christopher Richard Fawcett, London (GB); Mohammad Sharif, Middlesbrough (GB); Michael William Marshall Tuck, London (GB); David John Watson, London (GB); Michael Anthony Wood, Yarm (GB)

(73) Assignee: Davy Process Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/806,180

(22) PCT Filed: Sep. 29, 1999

(86) PCT No.: PCT/GB99/03226

§ 371 (c)(1),
(2), (4) Date: Jun. 5, 2001

(87) PCT Pub. No.: WO00/20373

PCT Pub. Date: Apr. 13, 2000

(30) Foreign Application Priority Data

Oct. 1, 1998 (EP) ................... 98308010

(51) Int. Cl.
  *B01D 3/00* (2006.01)
  *C07C 45/82* (2006.01)
  *C07C 67/54* (2006.01)
(52) U.S. Cl. ................ 203/14; 203/19; 203/75; 203/77; 203/78; 203/80; 560/248; 568/890; 568/913; 568/916

(58) Field of Classification Search ............ 203/14, 203/19, 75, 77, 78, 80; 560/248; 258/890, 258/913, 916
See application file for complete search history.

(56) References Cited

U.S. PATENT DOCUMENTS 1,708,460 A    4/1929   Zeisberg (Continued)

FOREIGN PATENT DOCUMENTS

EP         0 151 886 A1    8/1985

(Continued)

OTHER PUBLICATIONS

International Search Report for International Application No. PCT/GB 99/03226, mailed Jan. 14, 2000.

(Continued)

*Primary Examiner*—Virginia Manoharan
(74) *Attorney, Agent, or Firm*—Senniger Powers LLP (57) ABSTRACT

A process is described for the recovery of substantially pure ethyl acetate from a feedstock including ethyl acetate, ethanol and water. The process includes supplying the feedstock to a first distillation zone maintained under first distillation conditions effective for distilling from the feedstock a first distillate including ethyl acetate, ethanol, and less than about 10 mol % water. The first distillate is recovered from the first distillation zone and is supplied to a second distillation zone maintained under second distillation conditions, which include use of a higher pressure than that of the first distillation zone. The second distillation conditions are effective for distilling from the first distillate a second distillate including ethanol, water, and a minor proportion of ethyl acetate and yielding a substantially pure ethyl acetate bottom product, which is recovered. The second distillate is returned to the first distillation zone.

13 Claims, 3 Drawing Sheets

U.S. PATENT DOCUMENTS

| | | | |
|---|---|---|---|
| 2,027,182 | A | 1/1936 | Lazier |
| 2,524,899 | A | 10/1950 | Dunn |
| 3,714,236 | A | 1/1973 | Wright, Jr. et al. |
| 4,052,424 | A | 10/1977 | Vanderspurt |
| 4,220,803 | A | 9/1980 | Marcinkowsky et al. |
| 4,379,028 | A | 4/1983 | Berg et al. |
| 4,395,576 | A | 7/1983 | Kwantes et al. |
| 4,440,946 | A | 4/1984 | Summerville et al. |
| 4,481,146 | A | 11/1984 | Leupold et al. |
| 4,523,027 | A | 6/1985 | Kummer et al. |
| 4,569,726 | A | 2/1986 | Berg et al. |
| 4,613,701 | A | 9/1986 | Strong |
| 4,946,029 | A | 8/1990 | Frank et al. |
| 5,334,751 | A | 8/1994 | Lemanski et al. |
| 5,426,207 | A * | 6/1995 | Harrison et al. ............. 558/274 |
| 6,632,330 | B1 * | 10/2003 | Colley et al. .................. 203/29 |
| 6,809,217 | B1 | 10/2004 | Colley et al. |

FOREIGN PATENT DOCUMENTS

| | | | |
|---|---|---|---|
| EP | 0 201 105 | A1 | 11/1986 |
| GB | 287846 | * | 4/1929 |
| GB | 312345 | * | 8/1930 |
| GB | 470773 | | 8/1937 |
| JP | 59-25334 | | 2/1984 |
| JP | 5-186392 | | 7/1993 |
| SU | 362814 | | 11/1973 |
| WO | WO 00/20375 | A1 | 4/2000 |

OTHER PUBLICATIONS

Breitner, Edith, et al., Low Pressure Hydrogenation of Ketones with Platinum Metal Catalysts, Hydrogenation Carbonyl Compounds Over Platinum Metal Catalyst, [reprinted from the Journal of Organic Chemistry, 24, 1855 (1959)], pp. 1-3.

Engelhard Catalysts, Summary, 1977, 2 pages.

Engelhard Industries Division, Hydrogenation of Carbonyl Compounds Over Platinum Metal Catalysts, undated, 2 pages.

Fair, James R., Distillation, excerpt from Kirk-Othmer Encyclopedia of Chemical Technology 1993, 10 pages.

Grootendorst, E.J., et al., Selective Reduction of Acetic Acid to Acetaldehyde on Iron Oxides, Journal of Catalysis, 1994, pp. 261-269, vol. 148.

Matar, Sami, et al., Catalysis in Petrochemical Processes, 1989, p. 260, Kluwer Academic Publishers.

Nakumura, Shigeaki, et al., The Catalytic Dehydrogenation of Alcohols with Reduced Copper under Ultraviolet Light, Bulletin of the Chemical Society of Japan, 1971, pp. 1072-1078, vol. 44, No. 4.

Rylander, Paul N., Catalytic Hydrogenation over Platinum Metals, 1967, p. 245, Academic Press, New York and London.

Stiles, Alvin B., Catalyst Supports and Supported Catalysts, 1987, p. 132, Butterworth Publishers, Stoneham, MA.

Takeshita, Kenji, et al., Reduced Copper Catalyzed Conversion of Primary Alcohols into Esters and Ketones, Bulletin of the Chemical Society of Japan, 1978, pp. 2622-2627, vol. 51, No. 9.

Heterogeneous Catalysis, Products and Services Brochure, 1981-1984, Johnson Matthey Chemicals Limited, Orchard Road, Royston, Hertfordshire SGB 5HE, England, 6 pgs.

Abstract of Brazilian Application No. PI 9104652A, dated Apr. 27, 1993.

* cited by examiner

FIG 1

PROCESS

This invention relates to a process for the recovery of substantially pure ethyl acetate from a mixture comprising ethyl acetate, ethanol and water.

Separation of ethyl acetate from a composition comprising ethyl acetate, ethanol and water is disclosed in JP-A-05/186392 by feeding the composition to a distillation column to obtain a quasi-azeotropic mixture comprising ethyl acetate, ethanol and water, condensing it, separating the condensate into an organic layer and an aqueous layer, returning the organic layer to the column, and recovering ethyl acetate as a bottom product from the column.

It is difficult to separate a mixture comprising ethyl acetate, ethanol and water so as to recover substantially pure ethyl acetate therefrom because the boiling points of ethyl acetate and ethanol lie close to one another and both compounds form a binary azeotrope with ethyl acetate whose boiling points are close to that of ethyl acetate. In addition ethyl acetate, ethanol and water form a ternary azeotrope whose boiling point is also close to that of ethyl acetate.

Extractive distillation has been proposed in the prior art for separating ethyl acetate from ethanol and water. Use of an extraction agent comprising polyethylene glycol, diethylene glycol, or triethylene glycol for this purpose has been described in U.S. Pat. No. 4,569,726, while use of an extractive agent comprising dimethyl sulphoxide for the same purpose has been suggested in U.S. Pat. No. 4,379,028.

It is known that pressure-sensitive distillation (or pressure swing distillation, as it is sometimes called) can be used to break azeotropes. A review of this technique has been published: "Optimize Pressure-Sensitive Distillation", by Benjamin A. Harvitz, Chemical Engineering Progress, April 1997, pages 47 to 52. In his discussion of pressure-swing distillation (PSD) the author of this review states on page 47: "But, first, let's be clear about the basic concept behind PSD: it exploits the change in imposition of a binary azeotrope with pressure" He continues: "PSD, of course, is no panacea. For many systems (for instance, ethanol/water), azeotropic composition varies little, if at all, with pressure. This eliminates PSD as a viable option for separation of the components". A further article "Break Azeotropes with Pressure-Sensitive Distillation" by Timothy C. Frank, appeared in Chemical Engineering Progress, April 1997, pages 53 to 63. This states: "Well known, commercially viable applications of PSD include the separation of tetrahydrofuran (THF)/water, acetonitrile/water, methanol/methyl ethyl ketone (MEK), and acetone/methanol."

For further teaching regarding use of PSD to break binary azeotropes reference may be made to U.S. Pat. No. 4,362,603 and U.S. Pat. No. 5,346,595.

The PSD technique has also been proposed for separation of certain mixtures containing three or more components. Thus in U.S. Pat. No. 5,679,872 a process is described for the purification of an ether formed from an aliphatic monoalcohol containing at least two carbon atoms and an isoolefin containing at least four carbon atoms from a mixture containing said ether, said monoalcohol and hydrocarbons containing the same number of carbon atoms as that in the isoolefin. In this process the mixture is introduced into a first distillation zone from which almost all of the hydrocarbons are recovered overhead and the purified ether (for example, ethyl t-butyl ether) is recovered from the bottom, while at least one phase is extracted as a side stream from the first distillation zone and sent to a second distillation zone operating at a lower pressure to that of the first distillation zone, purified monoalcohol being recovered from the bottom and a mixture of monoalcohol, ether and hydrocarbons being recovered as an overhead effluent and recycled to the first distillation zone.

The PSD technique has also been proposed for separation of certain mixtures containing three or more components. Thus in U.S. Pat. No. 5,679,872 a process is described for the purification of an ether formed from on aliphatic monoalcohol containing at least two carbon atoms and an isoolefin containing at least four carbon atoms from a mixture containing said ether, said monoalcohol and hydrocarbons containing the same number of carbon atoms as that in the isoolefin. In this process the mixture is introduced into a first distillation zone from which almost all of the hydrocarbons are recovered overhead and the purified ether (for example, ethyl t-butyl ether) is recovered from the bottom, while at least one phase is extracted as a side stream from the first distillation zone and sent to a second distillation zone operating at a lower pressure to that of the first distillation zone, purified monoalcohol being recovered from the bottom and a mixture of monoalcohol, ether and hydrocarbons being recovered as an overhead effluent and recycled to the first distillation zone.

The present invention seeks to provide a novel process for the recovery of substantially pure ethyl acetate from a mixture comprising ethyl acetate, ethanol and water. It further seeks to provide a process enabling the recovery of substantially pure ethyl acetate from a complex mixture containing, in addition to ethyl acetate, also water and ethanol and possibly other minor components. In addition it seeks to provide a process for the recovery of substantially pure ethyl acetate from a mixture containing ethyl acetate, ethanol and water without the need for added solvents such as are needed in extractive distillation. Yet again it seeks to provide a process for obtaining ethyl acetate with a purity of greater than 99.5 mol % from a mixture comprising ethyl acetate, water and ethanol.

According to the present invention there is provided a process for the recovery of substantially pure ethyl acetate from a feedstock comprising ethyl acetate, ethanol and water which comprises:

(a) providing a first distillation zone maintained under distillation conditions which include use of a first distillation pressure, which are effective for distillation from a mixture comprising ethyl acetate, ethanol and water of a first distillate comprising ethyl acetate, ethanol, and not more than 10 mol % water, and which yield an ethanol rich bottom product comprising ethanol and water;

(b) providing a second distillation zone maintained under distillation conditions which include use of a second distillation pressure higher than the first distillation pressure, which are effective for distillation from a mixture comprising ethyl acetate, ethanol and water of a second distillate comprising ethanol, water, and a minor proportion of ethyl acetate, and which yield a substantially pure ethyl acetate bottom product;

(c) supplying to a zone selected from the first distillation zone and the second distillation zone a feedstock comprising ethyl acetate, ethanol and water;

(d) recovering a first distillate comprising ethyl acetate, ethanol, and not more than about 10 mol % water from the first distillation zone;

(e) supplying material of the first distillate to the second distillation zone;

(f) recovering an ethanol rich bottom product comprising ethanol and water from the first distillation zone;

(g) recovering a substantially pure ethyl acetate bottom product from the second distillation zone;

(h) recovering a second distillate comprising ethanol, water, and a minor proportion of ethyl acetate from the second distillation zone; and (i) recycling material of the second distillate of step (h) to the first distillation zone.

Ethanol, water and ethyl acetate form a minimum boiling ternary azeotrope upon distillation thereof. In addition mixtures of ethanol and ethyl acetate can form a binary azeotrope, as can not only mixtures of ethyl acetate and water but also mixtures of ethanol and water. Hence the separation of such mixtures can be extremely difficult when recovery of at least one component in substantially pure form is desired.

In the process of the invention distillation is carried out by a procedure which takes advantage of the fact that the composition of the minimum boiling ternary azeotrope formed by ethanol, water and ethyl acetate depends upon the pressure at which distillation is effected.

The feedstock is supplied either to the first distillation zone or to the second distillation zone, in dependence upon its composition. In some cases it is beneficial to supply the feedstock to the first distillation zone because this enables the flow rate of the first distillate, and hence also the corresponding flow rate of the second distillate, to be reduced to an optimum low value. By reducing these flow rates as far as possible, the heat requirements for operation of the two distillation zones can be correspondingly reduced. Thus when, for example, the water content of the feedstock is low, for example, when it is less than about 20 mol %, it will usually be more expedient to supply it to the first distillation zone. However, when the feedstock has a high water content, it may be more expedient to supply it to the second distillation zone because in that case the flow rate of the first distillate, and hence also the flow rate of the second distillate, can be reduced to optimum minimum values.

The process of the invention involves production of a first distillate containing ethyl acetate, ethanol, and less than about 10 mol % water in the first distillation zone, as well as production of a second distillate containing ethanol, water and a minor proportion (i.e. less than 50 mol %) of ethyl acetate in the second distillation zone.

In this process the first distillation zone is operated at a pressure which is less than that at which the second distillation zone is operated. The first distillation zone is preferably operated at a pressure of less than about 4 bar ($4 \times 10^5$ Pa), preferably from about 1 bar ($10^5$ Pa) to about 2 bar ($2 \times 10^5$ Pa), while the second distillation zone is operated at a higher pressure than that of the first distillation zone, for example at a pressure of from about 4 bar ($4 \times 10^5$ Pa) to about 25 bar ($2.5 \times 10^6$ Pa), preferably from about 9 bar ($9 \times 10^5$ Pa) to about 15 bar ($1.5 \times 10^6$ Pa).

It can be shown that in this distillation procedure the rate of flow of the first distillate from the first distillation zone to the second distillation zone and the corresponding flow rate from the second distillation zone to the first distillation zone of the second distillate can be minimised by designing and operating one of the distillation zones so that the relevant distillate formed in that zone has a composition very close to that of the ternary azeotrope at that pressure. However, in order to operate that zone so that the relevant distillate has a composition close to that of the ternary azeotrope at its pressure of operation, a high degree of separation is required which necessitates use of a distillation column with many distillation trays and a high heat input. In addition, since water has the highest latent heat of vaporization out of the three components of the ternary azeotrope, the total heat input to the two zones can be minimised by minimising the water content of the feeds to the distillation zones. Accordingly it is preferred to operate the process so that the amount of water in the first distillate, and hence the corresponding amount of water in the second distillate, shall be as low as practicably possible, i.e. less than about 6 mol % and preferably less than about 2 mol %.

In addition to forming a ternary azeotrope, the three components of the ternary azeotrope can also form binary azeotropes with one of the other components. For example, ethanol forms a binary azeotrope with water and also with ethyl acetate. It is preferred to select a pressure of operation of the second distillation zone so that the binary azeotrope between ethanol and ethyl acetate at that pressure has a lower ethyl acetate content than the ternary azeotrope at that pressure and further to select a pressure of operation for the first distillation zone and to adjust the flow rates of the distillates between the distillation zones so that the first distillate has as low a water content as possible. In this way the second distillate recovered from the second distillation zone will have a low content of ethyl acetate and, in addition, the heat input requirements for the two distillation zones can be kept as low as possible.

The feedstock will typically contain less than about 20 mol % water, and preferably less than about 15 mol % water, in which case it will preferably be supplied to the first distillation zone. In addition to ethyl acetate, ethanol and water it may further contain "light" components.

In a particularly preferred process an ethanol rich stream containing substantially all of the water in the feedstock is recovered from a bottom part of the first distillation zone, while an overhead stream that contains "light" components present in the feedstock supplied to the first distillation zone is recovered from the first distillation zone, and the first distillate is recovered as a liquid draw stream from an upper region of the first distillation zone. By the term "light" components is meant components that have lower boiling points than ethyl acetate and its azeotropes with water and ethanol.

The overhead stream from the first distillation zone contains "light" components present in the feedstock, such as diethyl ether, acetaldehyde and acetone. It can be burnt as a fuel.

The ethanol rich stream recovered from the bottom of the first distillation zone will contain any "heavies", i.e. products, including unknown products, with high boiling points compared to those of ethanol and ethyl acetate. These can be separated from the ethanol and water by distillation, if desired, prior to effecting removal of water from the resulting distillate. One suitable method for removal of water from the ethanol rich stream or from the distillate resulting from "heavies" removal is molecular sieve adsorption. Azeotropic distillation with a suitable entrainment agent, such as benzene, can alternatively be used. Membranes are currently under development which will enable separation of water from ethanol; these are reported to be nearly ready for commercial exploitation. Hence use of a membrane is another option available for separating water from the ethanol rich stream.

Preferably the water content of the thus produced relatively dry ethanol is less than about 5 mol %, and preferably less than about 2 mol %.

The first distillation zone will normally be provided with a plurality of trays, and the first distillate taken from a tray of the first distillation zone upon which the respective liquid composition has a water content of less than about 10 mol %, preferably less than about 6 mol %, e.g. from about 1 mol % to about 6 mol %.

The first distillate comprises from about 1 mol % to about 6 mol % water, from about 40 mol % to about 55 mol % ethyl acetate, not more than about 2 mol % other products (preferably not more than about 1 mol % other products) and the balance ethanol. Thus it may typically contain about 45 mol % ethyl acetate, about 50 mol % ethanol, about 4 mol % water and about 1 mol % other components. This first distillate is then passed to the second distillation zone (which is typically operated at a pressure of from about 4 bar ($4 \times 10^5$ Pa) to about 25 bar ($2.5 \times 10^6$ Pa), preferably at a pressure of from about 9 bar ($9 \times 10^5$ bar) to about 15 bar ($1.5 \times 10^6$ Pa).

The second distillate can be recovered as an overhead stream from the second distillation zone, while a bottom product comprising ethyl acetate is recovered from a bottom part of the second distillation zone. The second distillate can be returned to the first distillation zone at a point above the feed point of the feedstock supplied to the first distillation zone. The second distillate typically contains about 25 mol % ethyl acetate, about 68 mol % ethanol, about 6 mol % water, and about 1 mol % other components. The bottom product from the second distillation zone typically contains from about 99.8 mol % to about 99.95 mol % ethyl acetate. This bottom product can be re-distilled, if desired.

The compositions of the first and second distillates will depend upon the composition of the feedstock, upon the design of the distillation column or columns forming the respective distillation zone (in particular, upon the number of theoretical stages in the column), upon the heat supplied for reboiling purposes, and upon the pressure of operation. Hence the number of theoretical stages must be sufficient to allow a first distillate of the desired composition, i.e. one with a low water content (preferably less than about 6 mol %), to be formed at the respective design operating pressure. Similarly the second distillation zone must be designed to have sufficient theoretical stages to permit separation of a second distillate of the desired composition, also with a low water content, and the formation of a substantially pure ethyl acetate bottom product. Although it might be expected that it would be beneficial to design the first distillation zone so that the first distillate has a composition which is close to or at the composition of the ternary azeotrope at the operating pressure of the first distillation zone, this surprisingly proves not to be the case. Instead it is better to design the first distillation zone such that the first distillate has a composition which has as low a water content as is practicable. Not only can the heat input to the first distillation zone be substantially minimised in this way but also the distillation column or columns constituting the first distillation zone requires or require a reduced number of theoretical distillation stages. Hence both operating costs and construction costs can be minimised. In addition operation so that the first distillate has a composition near the ternary azeotrope is somewhat tricky to achieve because the composition of the distillate can readily change significantly with minor variations in operating conditions. Hence it may be difficult to achieve stable operation of the first and second distillation zones under such conditions. On the other hand operation of the first distillation zone under conditions such that the water content of the first distillate is as low as practicable proves not to be so susceptible to minor changes in operating conditions so that stable operation of the plant is more readily achieved.

The feedstock used in the process of the present invention should be free from compounds, such as acetaldehyde, n-butyraldehyde and butan-2-one, whose presence in the feedstock would cause separation problems if the feedstock were to be directly refined because their boiling points are close to that of ethyl acetate and because ethyl acetate tends to form distillates or azeotropes with such compounds. In order to minimise problems due to the presence of such compounds in the process of the invention, even in amounts as small as about 0.1 mol % or less, e.g. about 0.01 mol % or less, they can be removed by selective hydrogenation using a suitable selective hydrogenation catalyst, as described in our co-pending International Patent Applications Nos. PCT/GB 99/03230 (International Publication No. WO-A-00/20375) and PCT/GB 99/03228 (International Publication No. WO-A-00/20374) filed simultaneously herewith.

In the process of the invention the second distillate, which has a typical composition of about 25 mol % ethyl acetate, about 68 mol % ethanol, about 6 mol % water, and about 1 mol % of other components, is recovered as an overhead stream from the second distillation zone, while a bottom product comprising ethyl acetate is recovered from the second distillation zone which typically contains from about 99.8 mol % to about 99.95 mol % ethyl acetate; this second distillate is returned to the first distillation zone. If the feedstock is supplied to the first distillation zone, then the second distallate is preferably returned to the first distillation zone at a point above the feed point of the feedstock. The bottom product can, if desired, be re-distilled if a higher purity ethyl acetate product is required.

In order that the invention may be clearly understood and readily carried into effect, a preferred form of plant for the production of ethyl acetate, and a process in accordance with the invention will now be described, by way of example only, with reference to the accompanying drawings, wherein:—

Figure 1:
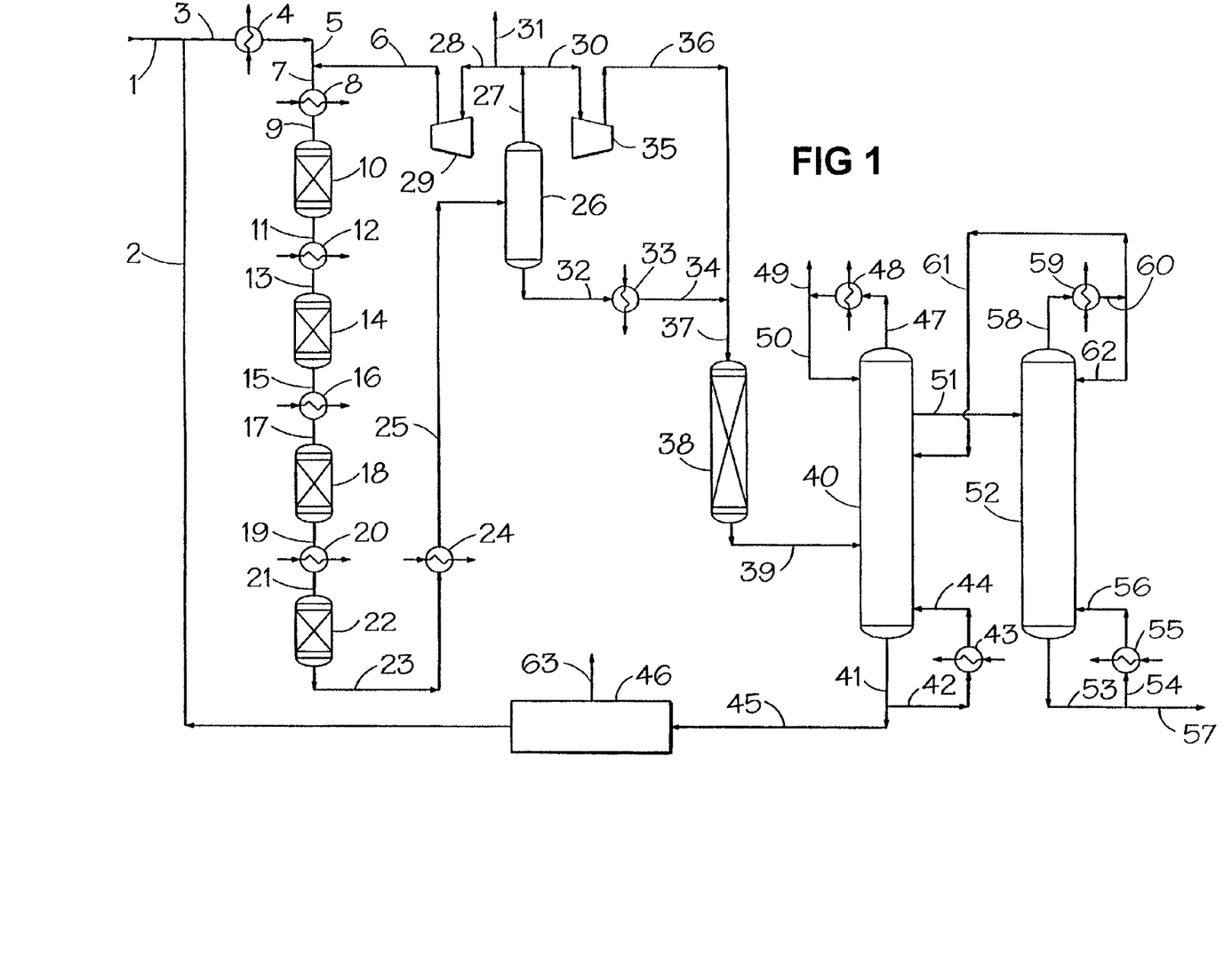
FIG. 1 is a flow diagram of a plant for the production of ethyl acetate constructed to operate a process in accordance with the invention.

Referring to FIG. 1 of the drawings, it will be appreciated by those skilled in the art that, since the drawing is diagrammatic, many conventional items of equipment, such as pumps, surge drums, flash drums, heat exchangers, temperature controllers, pressure controllers, holding tanks, temperature gauges, pressure gauges, and the like, which would be required in an operating plant, have been omitted for the sake of simplicity. Such items of equipment would be incorporated in an actual plant in accordance with standard chemical engineering practice and form no part of the present invention. Moreover there are many ways of effecting heat exchange and the depiction of separate heat exchangers each with its own heating or cooling line does not necessarily mean that single heat exchanger units are necessary. Indeed in many cases it may be more practicable and economic to use two separate heat exchangers instead of one with a step change in temperature occurring in each. It is also practicable to use conventional heat recovery techniques so as to recover heat from, or to increase the temperature of, one stream by heat exchange with another stream of the plant.

In the plant of FIG. 1 a stream of crude ethanol is pumped to the plant from a suitable holding tank (not shown) in line 1 at a pressure of 16.2 bar absolute ($16.2 \times 10^5$ Pa) and at a temperature of approximately 30° C. and is admixed with recycled material from line 2. The resulting mixture in line 3 is heated by means of heat exchanger 4 to a temperature of 166° C. thereby forming a vaporous stream which passes on in line 5 to be mixed with a stream of hydrogen from line 6. The resulting mixture passes on in line 7, is superheated in superheater 8 using high pressure steam, and exits it in line 9 at a pressure of 14.8 bar absolute ($14.8 \times 10^5$ Pa) and at a temperature of 235° C. Line 9 leads to a first dehydrogenation reactor 10 which contains a charge of a reduced copper oxide catalyst. A suitable catalyst is that sold under the designation E408Tu by Mallinckrodt Specialty Chemicals, Inc. In passage through first dehydrogenation reactor 10 the mixture of ethanol and hydrogen is partly converted by dehydrogenation according to equation (3) above to form ethyl acetate. This dehydrogenation reaction is endothermic.

The first intermediate dehydrogenation mixture exits reactor 10 in line 11 at a temperature in the range of from 205° C. to 220° C. and is reheated in heater 12 under the influence of high pressure steam. The reheated mixture flows on in line 13 to a second dehydrogenation reactor 14 which also contains a charge of the same dehydrogenation catalyst as that in reactor 10. Further dehydrogenation of ethanol to ethyl acetate occurs in passage through second dehydrogenation reactor 14.

A second intermediate dehydrogenation mixture containing ethyl acetate, unreacted ethanol and hydrogen exits reactor 14 in line 15 and is reheated in reheater 16 which is heated by means of high pressure steam. The reheated stream flows on in line 17 to a third dehydrogenation reactor 18 which contains a charge of the same dehydrogenation catalyst as is present in reactors 10 and 14.

The resulting third intermediate reaction mixture flows on in line 19 to heat exchanger 20 which is also heated by means of high pressure steam. The reheated mixture passes on in line 21 to fourth dehydrogenation reactor 22 which contains a further charge of the same dehydrogenation catalyst that is loaded into the first, second and third dehydrogenation reactors 10, 14, and 18.

A crude product mixture exits fourth dehydrogenation reactor 22 in line 23, is cooled in passage through a heat exchanger 24, and emerges in line 25 at a temperature of 60° C. and at a pressure of 11.3 bar ($11.3 \times 10^5$ Pa) absolute.

The crude product mixture in line 25 comprises hydrogen, ethyl acetate, unconverted ethanol, water and minor amounts of impurities present either from contamination in the feed or recycle streams or from side reactions in reactors 10, 14, 18 and 22. Examples of these impurities include iso-propanol, acetaldehyde, diethyl ether, methanol, acetone, di-iso-propyl ether, n-butyraldehyde, butan-2-one, sec-butanol, iso-propyl acetate, pentan-2-one, n-butanol, sec-pentanol, sec-butyl acetate, ethyl butyrate, n-butyl acetate and di-n-butyl ether. Of particular significance in relation to this invention are those impurities whose boiling points are close to that of ethyl acetate or which form azeotropic mixtures with ethyl acetate. These include ethanol, as well as certain carbonyl-containing compounds such as acetone, acetaldehyde and butan-2-one.

The crude mixture in line 25 flows into a knockout pot 26 which is provided with a condenser (not shown) supplied with chilled coolant. The uncondensed gases, which are now at a temperature of −10° C., are recovered in line 27. A part of these gases is recycled in line 28 and compressed by means of gas recycle compressor 29 to a pressure of 15.5 bar ($1.55 \times 10^6$ Pa) absolute to form the gas stream in line 6 for supply to the first dehydrogenation reactor 10. Another part is taken in line 30 for a purpose which will be described hereunder. A purge stream is taken in line 31.

The condensate is removed from knockout pot 26 in line 32 and is pumped by a pump (not shown) to heat exchanger 33. The resulting re-heated liquid, now at a temperature of 60° C. to 80° C., is fed via line 34 and mixed with a hydrogen-containing gas which is at a temperature of 119° C. and has been compressed by a second gas compressor 35 to a pressure of 43.1 bar ($4.31 \times 10^6$ Pa) absolute so as to pass along line 36. The resulting mixture flows on in line 37 into a reactor 38 which contains a charge of a selective hydrogenation catalyst which is chosen so as selectively to hydrogenate reactive carbonyl-containing compounds, such as n-butyraldehyde, butan-2-one and the like, to the respective corresponding alcohols but not to effect any significant hydrogenation of ethyl acetate to ethanol. The inlet temperature to reactor 37 is adjusted as necessary to a temperature in the range of from 60° C. to 80° C. in dependence upon the degree of deactivation of the catalyst but is chosen to be as low as possible consistent with obtaining an acceptable reaction rate because the equilibrium is favourable at lower temperatures than at high temperatures. A preferred catalyst is 5% ruthenium on carbon available from Englehard.

The resulting selectively hydrogenated reaction product is now essentially free from reactive carbonyl compounds, such as aldehydes and ketones, and exits reactor 38, in admixture with unreacted hydrogen, in line 39 at a temperature of 70° C. to 90° C. This line leads to a lower part of a first distillation column 40 which is maintained at a pressure of 1.5 bar ($1 \times 10^5$ Pa) absolute. A bottoms product is withdrawn from distillation column 40 in line 41. Part of this is recycled to distillation column through line 42, column reboiler 43 and line 44. The remainder is passed by way of line 45 to a purification section (or water removal package) 46 in which it is treated in any convenient manner for the removal of water (and possibly other impurities) therefrom so as to yield a stream of moderately dry ethanol for recycle to the first dehydrogenation reactor 10 by way of line 2. The precise design of water removal package 46 will depend upon the composition of the ethanol feed stream in line 1. The bottoms product in line 41 typically comprises mainly ethanol with minor amounts of, for example, iso-propanol, water, $C_{4+}$ alkanols, and traces of ketones, other esters and ethers.

An overhead stream, which typically comprises a major proportion of diethyl ether and lesser amounts of other ethers, methanol, ethanol, n-butyraldehyde, and alkanes, as well as traces of acetaldehyde, ethyl acetate, and water, is recovered in line 47 and condensed by means of condenser 48. Uncondensed gases are purged in line 49, while the resulting condensate is recycled to the top of distillation column 38 as a reflux stream in line 50. A side draw stream is taken from distillation column 40 in line 51 and pumped by a pump (not shown) to a second distillation column 52 which is maintained at an overhead pressure of 12 bar ($1.2 \times 10^6$ Pa) absolute.

From the bottom of distillation column 52 a stream comprising substantially pure ethyl acetate is recovered in line 53, part of which is recycled to a lower part of distillation column 52 by way of line 54, column reboiler 55, and line 56. The remainder forms the product stream in line 57 from the plant; this can be taken to storage or further distilled in one or more further distillation columns, if desired, in order to remove minor amounts of iso-propyl acetate, di-propyl ether, and 1-ethoxybutane.

An overhead product consisting mainly of ethanol, ethyl acetate and water, besides smaller amounts of 1-ethoxybutane, methanol, diethyl ether and di-propyl ether and traces of alkanes, is taken in line 58 and condensed by means of condenser 59. The resulting condensate passes on in line 60, some being recycled to the first distillation column by way of line 61 while the remainder is recycled as a reflux stream to the second distillation column 52 in line 62. Reference numeral 63 indicates a line for recovery of water and other materials from water removal package 46.

The compositions in mol % of some of the more important streams in the plant of FIG. 1 are set out in Table 1 below.

TABLE 1

| Stream | 1 | 2 | 9 | 25 | 27 | 32 | 37 | 39 | 45 | 49 | 51 | 57 | 61 | 63 |
|---|---|---|---|---|---|---|---|---|---|---|---|---|---|---|
| Hydrogen | 0.00 | 0.00 | 1.96 | 32.43 | 95.67 | 0.24 | 5.32 | 3.26 | 0.00 | 64.41 | 0.00 | 0.00 | 0.00 | 0.00 |
| Carbon monoxide | 0.00 | 0.00 | 0.01 | 0.17 | 0.49 | 0.00 | 0.03 | 0.03 | 0.00 | 0.64 | 0.00 | 0.00 | 0.00 | 0.00 |
| Water | 0.13 | 0.13 | 0.13 | 1.20 | 0.04 | 1.80 | 1.71 | 1.73 | 2.26 | 0.93 | 3.94 | 0.00 | 5.36 | 39.80 |
| Methanol | 0.01 | 0.00 | 0.01 | 0.01 | 0.00 | 0.01 | 0.01 | 0.01 | 0.00 | 0.20 | 0.06 | 0.00 | 0.09 | 0.00 |
| Ethanol | 99.84 | 99.84 | 97.82 | 49.25 | 1.39 | 73.50 | 69.67 | 72.70 | 96.52 | 16.76 | 50.42 | 0.02 | 68.73 | 37.90 |
| Ethyl acetate | 0.00 | 0.00 | 0.01 | 15.03 | 0.91 | 22.32 | 21.18 | 20.86 | 0.00 | 7.17 | 45.40 | 99.98 | 25.57 | 0.00 |
| Acetaldehyde | 0.00 | 0.00 | 0.00 | 0.51 | 0.03 | 0.75 | 0.71 | 0.01 | 0.00 | 0.13 | 0.14 | 0.00 | 0.19 | 0.00 |
| Ethane | 0.00 | 0.00 | 0.00 | 0.09 | 0.20 | 0.03 | 0.04 | 0.04 | 0.00 | 0.82 | 0.00 | 0.00 | 0.00 | 0.00 |
| Methane | 0.00 | 0.00 | 0.03 | 0.41 | 1.17 | 0.03 | 0.09 | 0.09 | 0.00 | 1.78 | 0.00 | 0.00 | 0.00 | 0.00 |
| Di-ethyl ether | 0.01 | 0.00 | 0.01 | 0.27 | 0.09 | 0.37 | 0.35 | 0.36 | 0.00 | 7.09 | 0.04 | 0.00 | 0.06 | 0.00 |
| n-butyraldehyde | 0.00 | 0.00 | 0.00 | 0.01 | 0.00 | 0.01 | 0.01 | 0.00 | 0.00 | 0.00 | 0.00 | 0.00 | 0.00 | 0.00 |
| n-butanol | 0.00 | 0.01 | 0.00 | 0.12 | 0.00 | 0.18 | 0.17 | 0.19 | 0.25 | 0.01 | 0.00 | 0.00 | 0.00 | 4.53 |
| sec-butanol | 0.00 | 0.01 | 0.00 | 0.26 | 0.00 | 0.38 | 0.36 | 0.51 | 0.67 | 0.05 | 0.00 | 0.00 | 0.00 | 12.15 |
| Butan-2-one | 0.01 | 0.00 | 0.01 | 0.10 | 0.01 | 0.14 | 0.14 | 0.00 | 0.00 | 0.00 | 0.00 | 0.00 | 0.00 | 0.00 |
| n-butyl acetate | 0.00 | 0.00 | 0.00 | 0.05 | 0.00 | 0.08 | 0.07 | 0.07 | 0.10 | 0.01 | 0.00 | 0.00 | 0.00 | 1.81 |
| sec-butyl acetate | 0.00 | 0.00 | 0.00 | 0.02 | 0.00 | 0.03 | 0.03 | 0.03 | 0.04 | 0.00 | 0.00 | 0.00 | 0.00 | 0.73 |
| Ethyl butyrate | 0.00 | 0.00 | 0.00 | 0.04 | 0.00 | 0.07 | 0.06 | 0.06 | 0.09 | 0.00 | 0.00 | 0.00 | 0.00 | 1.63 |
| Di-butyl ether | 0.00 | 0.00 | 0.00 | 0.00 | 0.00 | 0.01 | 0.01 | 0.01 | 0.01 | 0.00 | 0.00 | 0.00 | 0.00 | 0.18 |
| n-hexanol | 0.00 | 0.00 | 0.00 | 0.00 | 0.00 | 0.00 | 0.00 | 0.00 | 0.01 | 0.00 | 0.00 | 0.00 | 0.00 | 0.18 |
| iso-butanol | 0.00 | 0.01 | 0.01 | 0.01 | 0.00 | 0.01 | 0.01 | 0.01 | 0.01 | 0.00 | 0.00 | 0.00 | 0.00 | 0.18 |
| Others | 0.00 | 0.00 | 0.00 | 0.02 | 0.00 | 0.04 | 0.03 | 0.03 | 0.04 | 0.00 | 0.00 | 0.00 | 0.00 | 0.91 |
| Total | 100.00 | 100.00 | 100.00 | 100.00 | 100.00 | 100.00 | 100.00 | 100.00 | 100.00 | 100.00 | 100.00 | 100.00 | 100.00 | 100.00 |

Figure 2:
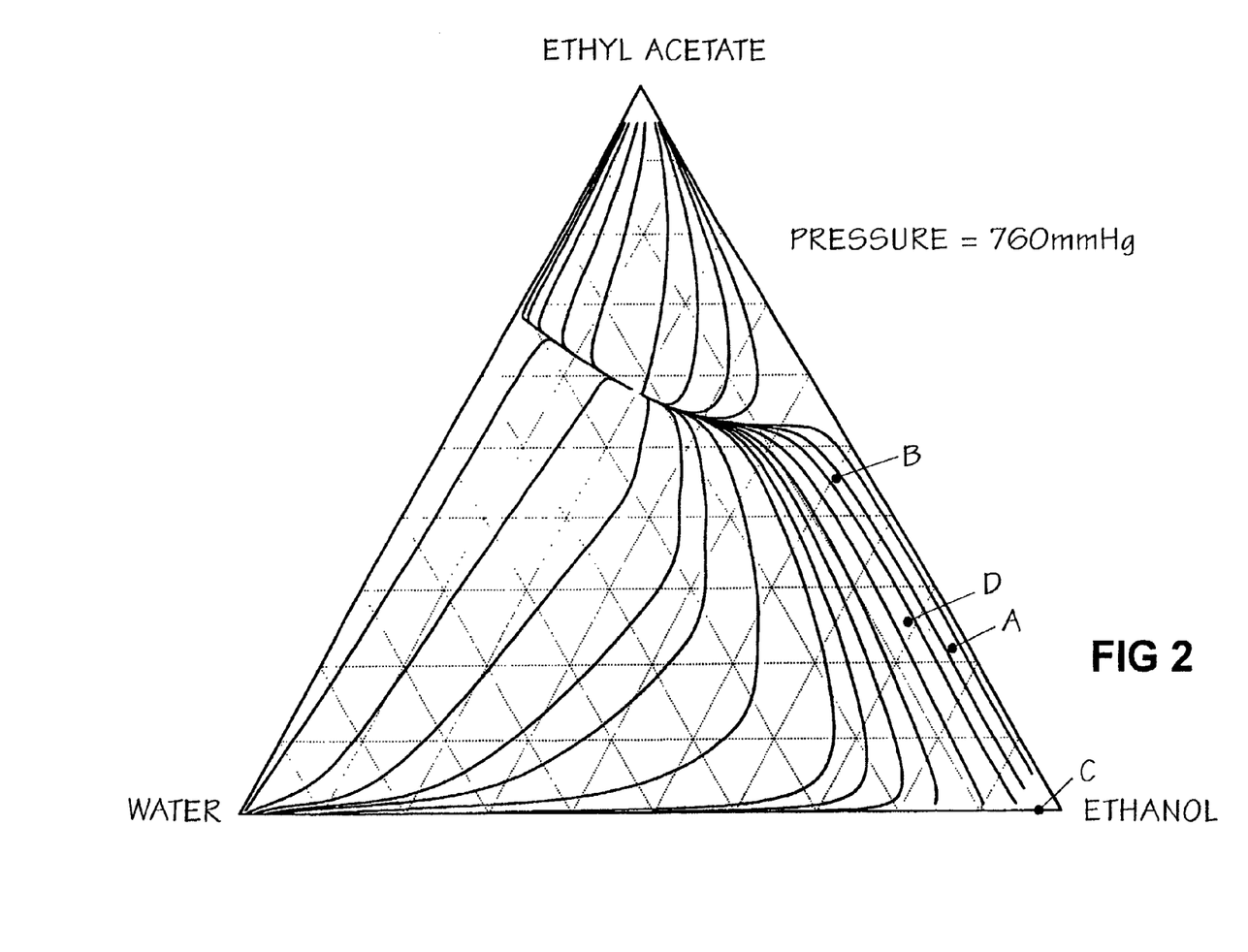
FIGS. 2 and 3 are triangular diagrams illustrating the boiling behaviour of ternary mixtures of ethanol, water and ethyl acetate at two different pressures.
Figure 3:
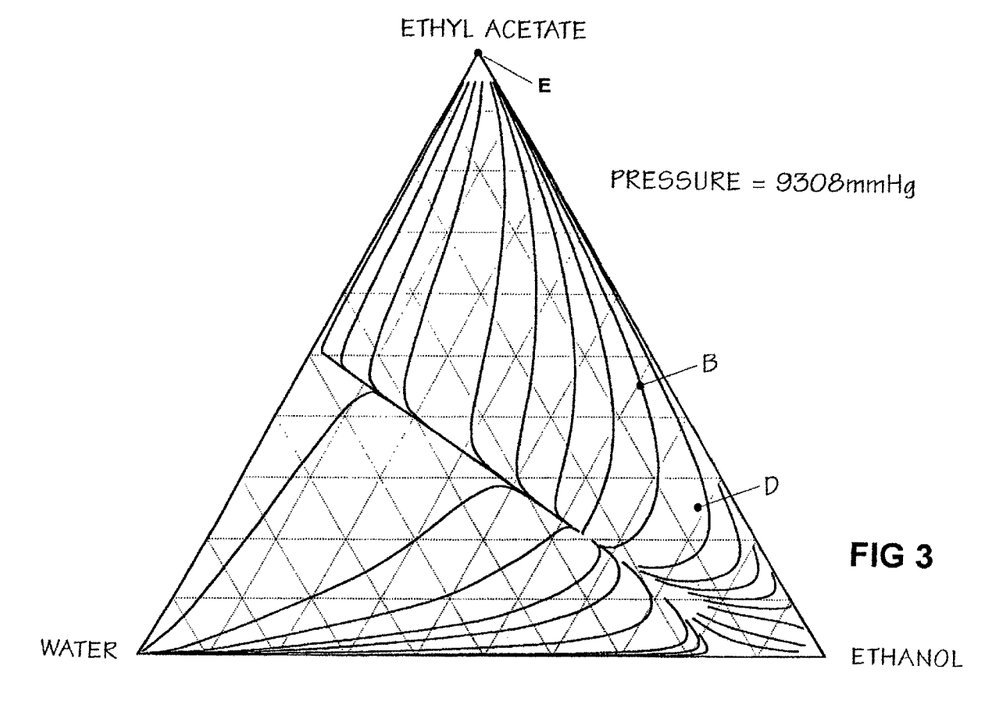

FIG. 2 is a triangular diagram illustrating the distillation characteristics of mixtures of ethanol, water and ethyl acetate at 760 mm Hg (1.01×10$^6$ Pa) in which are plotted distillation lines for different mixtures of the three components. FIG. 3 is a similar diagram illustrating the distillation characteristics of the same ternary system at 9308 mm Hg (12.41×10$^6$ Pa). It will be noted that there are significant differences between the distillation lines observed at different operating pressures. In FIG. 2 the composition of a typical feed as might be supplied in line 39 of the plant of FIG. 1 is indicated by point A. Point B indicates the composition of the side draw stream in line 51 for this feed. Point C indicates the composition of the resulting bottom stream in line 41 and point D indicates the composition of the stream in line 61. The effective feed composition to column 40 lies on the intersection of the straight line joining A and D with the straight line joining points B and C. In FIG. 3 the points B and D represents the same compositions as the corresponding points in the triangular diagram of FIG. 2. Point E represents the composition of the substantially pure ethyl acetate recovered in line 45.

The invention is further described in the following Examples.

EXAMPLES 1 TO 5

These Examples investigated the dehydrogenation of ethanol to ethyl acetate in the presence of hydrogen. The apparatus used included a dehydrogenation reactor made of stainless steel tubing which contained a charge of reduced copper oxide catalyst and which was immersed in a hot oil bath for heating purposes.

At start-up a charge of 200 ml of a tabulated copper oxide catalyst available under the designation E408Tu from Mallinckrodt Specialty Chemicals was placed in the reactor which was then purged with nitrogen at 14.5 bar (14.5×10$^5$ Pa). A dilute H$_2$ in N$_2$ gaseous mixture at 3 bar (3×10$^5$ Pa) was passed over the catalyst at a rate of 600 standard liters per hour for 60 hours in order to effect catalyst reduction. The oil bath was raised to the temperature indicated in Table 2 below. The gas feed was then changed to pure hydrogen.

In operation hydrogen was introduced to the dehydrogenation reactor at a rate of 2 standard liters per hour by way of a pressure regulator and flow controller through a line which was immersed in the bottom of the oil bath. An ethanol stream whose composition is set out in Table 2 was fed as a liquid at a rate of 200 ml/hr to a vaporizer and mixed with the hydrogen. The resulting vaporous mixture of ethanol and hydrogen was supplied to the dehydrogenation reactor.

The reaction product was cooled and the liquid condensate was analysed by gas chromatography. The results obtained are summarized in Table 2.

TABLE 2

| | | Example No | | | | |
|---|---|---|---|---|---|---|
| | Feed | 1 | 2 | 3 | 4 | 5 |
| Temperature (° C.) | — | 225 | 224 | 224 | 223 | 224 |
| Pressure (bar) [10$^5$ Pa] | — | 4.53 | 2.74 | 7.91 | 28.6 | 47.0 |
| Product Analysis (wt %) | | | | | | |
| Acetaldehyde | 0.007 | 2.578 | 5.317 | 1.388 | 0.114 | 0.027 |
| Methanol | 0.064 | 0.063 | 0.087 | 0.034 | 0.013 | 0.011 |
| Di-ethyl ether | 0.108 | 0.133 | 0.120 | 0.139 | 0.167 | 0.185 |
| Ethanol | 95.093 | 63.184 | 66.778 | 64.050 | 67.236 | 72.676 |
| Acetone | 0.007 | 2.264 | 2.883 | 1.679 | 0.630 | 0.326 |
| iso-propanol | 3.403 | 1.582 | 1.081 | 2.114 | 3.210 | 3.511 |
| Di-iso-propyl ether | 0.116 | 0.139 | 0.134 | 0.138 | 0.136 | 0.138 |
| n-butyraldehyde | 0 | 0.012 | 0.010 | 0.006 | 0.004 | 0.005 |
| Ethyl acetate | 0.030 | 25.605 | 18.935 | 27.087 | 26.377 | 21.107 |
| Butan-2-one | 0.005 | 1.230 | 1.655 | 0.661 | 0.074 | 0.015 |
| sec-butanol | 0.004 | 0.768 | 0.543 | 0.761 | 0.360 | 0.174 |
| iso-propyl acetate | 0 | 0.184 | 0.144 | 0.040 | 0.316 | 0.318 |
| Pentan-2-one | 0 | 0.316 | 0.309 | 0.233 | 0.055 | 0.010 |
| n-butanol | 0.097 | 0.329 | 0.410 | 0.274 | 0.203 | 0.431 |
| sec-pentanol | 0 | 0.138 | 0.075 | 0.180 | 0.148 | 0.087 |

TABLE 2-continued

| | Feed | Example No | | | | |
| | | 1 | 2 | 3 | 4 | 5 |
|---|---|---|---|---|---|---|
| sec-butyl acetate | 0 | 0.058 | 0.037 | 0.057 | 0.052 | 0.044 |
| Ethyl butyrate | 0 | 0.132 | 0.115 | 0.093 | 0.030 | 0.075 |
| n-butyl acetate | 0 | 0.123 | 0.096 | 0.086 | 0.022 | 0.076 |
| Water | 0.540 | 0.789 | 0.920 | 0.660 | 0.450 | 0.460 |
| Others | 0.526 | 0.373 | 0.351 | 0.320 | 0.403 | 0.324 |
| Total | 100.00 | 100.00 | 100.00 | 100.00 | 100.00 | 100.00 |

EXAMPLES 6 TO 9

In these Examples the selective hydrogenation of reactive carbonyl compounds in the presence of ethyl acetate was investigated using a hydrogenation reactor constructed out of stainless steel which was immersed in a hot oil bath for heating purposes.

In operation hydrogen was introduced by way of a pressure regulator and flow controller to the reactor which contained a charge of an Englehard 5% ruthenium on carbon granular catalyst.

At start up a charge of 100 ml of the granular catalyst was placed in the reactor which was then supplied with hydrogen at a pressure of 7.9 bar ($7.9 \times 10^5$ Pa), and warmed to 180-200° C. from room temperature at a rate of 20° C. per hour. The reactor was held at 180-200° C. for one hour and then cooled. At the end of this procedure the catalyst was fully reduced.

Dehydrogenation reaction product mixture whose composition is set out under "Feed" in Table 3 was introduced to a heater at a rate of 130 ml/hr and admixed with 7.8 standard liters per hour of hydrogen prior to admission to the selective hydrogenation reactor. The reaction product was cooled and the liquid condensate was analysed by gas chromatography. The results are summarized in Table 3.

TABLE 3

| | Feed | Example No | | | |
| | | 6 | 7 | 8 | 9 |
|---|---|---|---|---|---|
| Reactor Temperature (° C.) | — | 91 | 80 | 72 | 110 |
| Pressure (bar)[$10^5$ Pa] | — | 14.2 | 14.2 | 14.4 | 14.1 |
| Product Analysis (Wt %) | | | | | |
| Acetaldehyde | 0.904 | 0.034 | 0.040 | 0.038 | 0.039 |
| Diethyl ether | 0.579 | 0.428 | 0.418 | 0.417 | 0.419 |
| Ethanol | 68.223 | 70.040 | 70.121 | 70.163 | 70.301 |
| Acetone | 2.282 | trace | trace | trace | trace |
| iso-propanol | 1.004 | 3.232 | 3.233 | 3.213 | 3.231 |
| Di-iso-propyl ether | 0.003 | 0.098 | 0.097 | 0.097 | 0.097 |
| n-butyraldehyde | 0.010 | trace | trace | trace | trace |
| Ethyl acetate | 23.263 | 22.572 | 22.464 | 22.437 | 22.396 |
| Butan-2-one | 0.170 | 0.002 | 0.004 | 0.007 | 0.003 |
| sec-butanol | 0.371 | 0.567 | 0.566 | 0.560 | 0.567 |
| iso-propyl acetate | 0.186 | 0.185 | 0.184 | 0.184 | 0.184 |
| n-butanol | 0.507 | 0.730 | 0.770 | 0.776 | 0.570 |
| Water | 1.410 | 1.170 | 1.170 | 1.200 | 1.270 |
| Others | 1.088 | 0.942 | 0.933 | 0.908 | 0.923 |
| Total | 100.00 | 100.00 | 100.00 | 100.00 | 100.00 |

Notes: The increased amount of n-butanol noted in Examples 6 to 9 compared with the amount in the feed can be ascribed not only to n-butanol formed by hydrogenation of n-butyraldehyde present in the feed (the amount of which is, in any case, difficult to measure) but also from hydrogenation of other products which contain $C_4$ groups and which are included in the figure given for "others" in the feed.

EXAMPLES 10 TO 12

The general procedure of Examples 6 to 9 was repeated using a different feed and different reaction conditions. The results are set out in Table 4 below.

TABLE 4

| | Feed | Example No | | |
| | | 10 | 11 | 12 |
|---|---|---|---|---|
| Reactor Temperature (° C.) | — | 79 | 98 | 119 |
| Pressure (bar) [$10^5$ Pa] | — | 42.6 | 42.1 | 42.5 |
| Product Analysis (Wt %) | | | | |
| Acetaldehyde | 0.952 | 0.006 | 0.006 | 0.006 |
| Diethyl ether | 0.030 | 0.030 | 0.029 | 0.033 |
| Ethanol | 64.703 | 65.930 | 66.034 | 65.627 |
| Acetone | trace | 0 | 0 | 0 |
| iso-propanol | 0.022 | 0.032 | 0.035 | 0.038 |
| n-butyraldehyde | 0 | 0 | 0 | 0 |
| Ethyl acetate | 31.692 | 31.410 | 31.155 | 31.409 |
| Butan-2-one | 0.301 | trace | trace | 0.001 |
| sec-butanol | 0.487 | 0.803 | 0.806 | 0.810 |
| n-butanol | 0.560 | 0.588 | 0.596 | 0.573 |
| Water | 0.620 | 0.600 | 0.700 | 0.890 |
| Others | 0.633 | 0.601 | 0.639 | 0.613 |
| Total | 100.000 | 100.00 | 100.00 | 100.00 |

EXAMPLE 13

A mixture containing ethanol, water, ethyl acetate and other components was distilled in a continuous feed laboratory distillation apparatus having the general layout of columns 40 and 52 of FIG. 1, except that line 51 received condensate from line 50, rather than a side draw stream from an outlet positioned somewhat lower in column 40. A bleed of $O_2$-free nitrogen was supplied to column 40 so as to ensure that oxygen was excluded from column 40 in order to prevent oxidation of any oxygen-sensitive components in the feed in line 39 such as aldehydes. Hence column 40 was operated at a few millibars over atmospheric pressure. The feed to column 30 was vaporised in a stream of $O_2$-free nitrogen prior to introduction into column 40. The reflux temperature in column 40 was 64° C., the overhead temperature was 72° C. and the temperature at the bottom of the column was 73° C. The reflux ratio was 5:1. The operating pressure in column 52 was 12.4 bar ($1.24 \times 10^6$ Pa gauge). The overhead temperature was 160° C., the reflux temperature was 153° C. and the boiler temperature was 204° C. The reflux ratio was 2.8:1. The distillation column had 3 thermocouples positioned near the top, at the mid point and near the bottom, the readings of which were 163° C., 180° C. and 180° C. respectively. The results obtained are listed in Table in which amounts are in % by weight.

TABLE 5

| | Line No. | | | | |
| | 39 | 51 | 41 | 61 | 53 |
|---|---|---|---|---|---|
| Acetaldehyde | 0.009 | 0.007 | 0.013 | 0.446 | |
| Methanol | 0.090 | 0.141 | | 0.199 | |

TABLE 5-continued

| | 39 | 51 | 41 | 61 | 53 |
|---|---|---|---|---|---|
| Diethyl ether | 0.073 | 0.113 | | 0.226 | |
| Ethanol | 57.626 | 31.077 | 96.579 | 71.382 | 0.064 |
| iso-propanol | 0.027 | | 0.087 | | |
| Ethyl acetate | 40.514 | 68.021 | 0.018 | 24.811 | 99.890 |
| Butan-2-ol | 0.548 | | 1.499 | | |
| n-butanol | 0.192 | 0.021 | 0.519 | | 0.010 |
| Ethyl butyrate | 0.117 | | 0.307 | | |
| Butyl acetate | 0.136 | | 0.358 | | |
| Water | 0.550 | 0.590 | 0.330 | 2.920 | 0.010 |
| "Light" unknowns | 0.020 | 0.029 | | 0.003 | |
| "Heavy" unknowns | 0.098 | 0.001 | 0.290 | 0.013 | 0.026 |
| Total | 100.00 | 100.00 | 100.00 | 100.00 | 100.00 |

The invention claimed is:

1. A process for the recovery of purified ethyl acetate from a feedstock comprising ethyl acetate, ethanol and water which comprises:
- (a) operating a first distillation zone of a pressure-swing distillation system maintained under distillation conditions which include use of a first distillation pressure, which are effective for distillation from a mixture comprising ethyl acetate, ethanol and water of a first distillate comprising ethyl acetate, ethanol, and not more than 10 mol % water, and which yield an ethanol rich bottom product comprising ethanol and water;
- (b) operating a second distillation zone of the pressure-swing distillation system maintained under distillation conditions which include use of a second distillation pressure higher than the first distillation pressure, which are effective for distillation from a mixture comprising ethyl acetate, ethanol and water of a second distillate comprising ethanol, water, and a minor proportion of ethyl acetate, and which yield a purified ethyl acetate bottom product;
- (c) supplying to a zone selected from the first distillation zone and the second distillation zone a feedstock comprising ethyl acetate, ethanol and water;
- (d) recovering a first distillate comprising ethyl acetate, ethanol, and not more than about 10 mol % water from the first distillation zone;
- (e) supplying material of the first distillate to the second distillation zone;
- (f) recovering an ethanol rich bottom product comprising ethanol and water from the first distillation zone;
- (g) recovering a purified ethyl acetate bottom product from the second distillation zone;
- (h) recovering a second distillate comprising about 68 mol % ethanol, about 6 mol % water, about 25 mol % ethyl acetate and about 1 mol % other components from the second distillation zone; and
- (i) recycling material of the second distillate of step (h) to the first distillation zone.

2. A process according to claim 1, in which in step (c) the feedstock has a water content of less than about 20 mol % and is supplied to the first distillation zone.

3. A process according to claim 1, in which the first distillation zone is operated at a pressure of less than about 4 bar ($4 \times 10^5$ Pa).

4. A process according to claim 1, in which the first distillation zone is operated at a pressure of from about 1 bar ($10^5$ Pa) to about 2 bar ($2 \times 10^5$ Pa).

5. A process according to claim 1, in which the second distillation zone is operated at a pressure of from about 4 bar ($4 \times 10^5$ Pa) to about 25 bar ($2.5 \times 10^6$ Pa).

6. A process according to claim 1, in which the second distillation zone which is operated at a pressure of from about 9 bar ($9 \times 10^5$ bar) absolute to about 15 bar ($1.5 \times 10^6$ Pa) absolute.

7. A process according to claim 1, in which the first distillate has a water content of from about 1 mol % to about 6 mol %.

8. A process according to claim 1, in which the feedstock supplied to the first distillation zone further contains "light" components, in which an ethanol rich stream is recovered from a bottom part of the first distillation zone, in which an overhead stream that contains "light" components present in the mixture supplied to the first distillation zone is recovered from the first distillation zone, and in which the first distillate is recovered as a liquid draw stream from an upper region of the first distillation zone.

9. A process according to claim 8, in which the ethanol rich stream recovered from the bottom part of the first distillation zone is subjected to treatment for removal of water therefrom thereby to produce a relatively dry ethanol stream having a water content of less than about 5 mol %.

10. A process according to claim 1, in which the first distillate contains about 1 mol % to about 6 mol % water, from about 40 mol % to about 55 mol % ethyl acetate, not more than about 1 mol % other products, and the balance ethanol.

11. A process according to claim 1, in which the first distillate contains about 45 mol % ethyl acetate, about 50 mol % ethanol, about 4 mol % water and about 1 mol % other components.

12. A process according to claim 1, in which the second distillate is recovered as an overhead stream from the second distillation zone, in which a bottom product comprising ethyl acetate is recovered from the second distillation zone, and in which the second distillate is returned to the first distillation zone at a point above the feed point of the feedstock to the first distillation zone.

13. A process according to claim 1, in which the bottom product from the second distillation zone contains from about 99.8 mol % to about 99.95 mol % ethyl acetate.

* * * * *